United States Patent [19]

Van Lintel

[11] Patent Number: 5,759,014

[45] Date of Patent: Jun. 2, 1998

[54] MICROPUMP

[75] Inventor: Harald Van Lintel, Lausanne, Switzerland

[73] Assignee: Westonbridge International Limited, Dublin, Ireland

[21] Appl. No.: 676,146

[22] PCT Filed: Jan. 12, 1995

[86] PCT No.: PCT/IB95/00028

§ 371 Date: Jul. 29, 1996

§ 102(e) Date: Jul. 29, 1996

[87] PCT Pub. No.: WO95/19502

PCT Pub. Date: Jul. 20, 1995

[30] Foreign Application Priority Data

Jan. 14, 1994 [CH] Switzerland ............... 117/94

[51] Int. Cl.⁶ .............................................. F04B 17/00
[52] U.S. Cl. ............................ 417/413.3; 417/413.2
[58] Field of Search .................. 417/413.3, 413.2, 417/322

[56] References Cited

U.S. PATENT DOCUMENTS

| | | | |
|---|---|---|---|
| 5,224,843 | 7/1993 | Van Lintel | 417/413.3 |
| 5,271,724 | 12/1993 | Van Lintel | 417/413.3 |

FOREIGN PATENT DOCUMENTS

| | | |
|---|---|---|
| 0 025 005 | 3/1981 | European Pat. Off. . |
| 2 516 606 | 5/1983 | France . |
| 33 20 443 | 12/1984 | Germany . |
| 2 248 891 | 4/1992 | United Kingdom . |
| Wo 92/04569 | 3/1992 | WIPO . |

OTHER PUBLICATIONS

"Liquid Control Micro–Device", Nikkei Electronics (no. 480), Aug. 1989.

Smith, L., et al., "A Silicon Self–Aligned Non–Reverse Valve", *Transducers '91*, Jun., 1991, IEEE, pp. 1049–1051.

Van Lintel et al., "A Piezoelectric Micropump Based on Micromachining of Silicon", *Sensors and Actuators*, vol. 15, 1988, pp. 153–167.

*Primary Examiner*—Charles G. Freay
*Attorney, Agent, or Firm*—Young & Thompson

[57] ABSTRACT

A micropump including two glass wafers (2, 8) with a machined silicon wafer (6) sealingly inserted therebetween. An inlet valve (12), a pump chamber (14) and an outlet valve (16) are arranged between an inlet channel (4) and an outlet channel (5). A pump diaphragm (36) forming one wall of the pump chamber comprises a thicker central portion (38) operating like a piston. A piezoelectric element (52) acts on the diaphragm via an intermediate part (64) to provide the pumping movement. The pump chamber (14) and the spaces (22, 24) linking the pump chamber to the inlet and outlet valves are shaped so that the reduction in the inner volume of the micropump caused by a reduction in the volume of the pump chamber during the pumping movement is such that the air in the micropump is compressed to a pressure high enough to open the outlet valve, whereby the micropump is self-priming.

24 Claims, 3 Drawing Sheets

MICROPUMP

FIELD OF THE INVENTION

The present invention relates to a micropump comprising at least one base plate and a second plate secured to the base plate, so as to define a pumping chamber, inlet and outlet control members in direct connection with the pumping chamber, the control members being located on or in at least one of the two plates, at least one of these plates being machined by micromachining techniques by photolithography of a sealing material; an internal volume (Vi) comprising the volume of the pumping chamber and the volumes of the spaces for connection with the control members, the pumping chamber comprising a movable wall machined in one of the plates, actuation means being provided to display the movable wall to effect a periodic decrease and increase of the internal volume.

BACKGROUND OF THE INVENTION

Such pumps can be used particularly for the in situ administration of medications, the miniaturization of the pump permitting the sick person to carry it himself, even if desired to receive a pump directly implanted in the body. Moreover, such pumps permit the administration of small doses of the fluid to be injected.

In an article entitled "A piezoelectric micropump based on micromachining of silicon" which appeared in "Sensors and Actuators", No. 15 (1988), pp 153–157, H. Van Lintel et al. give a description of two embodiments of a micropump, each comprising a stack of three plates, which is to say a machined silicon plate disposed between two glass plates.

The silicon plate is incised to provide a cavity, which with one of the glass plates defines the pumping chamber, an inlet or suction valve and at least one outlet or discharge valve placing the pumping chamber in communication respectively with an inlet channel and an outlet channel. The portion of the wall forming a wall of the pumping chamber can be deformed by the control element constituted for example by a wafer or a piezoelectric crystal. The latter is provided with two electrodes which, when they are connected to a source of electrical voltage, effect the deformation of the wafer and, as a result, the deformation of the plate, which gives rise to a variation of volume of the pumping chamber. This movable or deformable wall of the pumping chamber can thus be displaced between two positions.

The operation of the micropump is as follows. When no electrical voltage is applied to the piezoelectric wafer, the inlet and outlet valves are in closed position. When an electrical voltage is applied, it produces an increase of pressure in the pumping chamber which gives rise to opening of the outlet valve. The fluid contained in the pumping chamber is then discharged through the outlet channel by the displacement of the deformable wall from a first position toward a second position. During this phase, the inlet valve is maintained closed by the pressure prevailing in the pumping chamber.

On the contrary, when the electrical voltage is decreased, the pressure in the pumping chamber decreases. This gives rise to closing of the outlet valve and opening the inlet valve. There is then a suction of the fluid into the pumping chamber through the inlet channel because of the displacement of the flexible wall from the second position toward the first position.

GB-A-2 248 891 showing the closest state of the art discloses a micropump of the same type as that previously described. In this micropump the inlet valve is however replaced by a flow limiter having a restricted flow cross section.

The operation of this type of micropump is greatly influenced by the compressibility of the fluid contained in the internal volume and in fact such a micropump does not operate if it contains too much air; the flow rate pumped is thus greatly decreased, even reduced to zero.

Similarly, the starting of such pumps is complicated and requires considerable apparatus, such as a vacuum pump, starting chamber or injection device. Because of this, starting cannot be effected other than in a specialized establishment or in the factory during manufacture.

Certain micropumps are moreover provided with a protective device against overpressure at the inlet, which prevents starting by application of an overpressure.

There is also known from DE-A-33 20 443 a pump comprising a metallic base plate in which are mounted two valves. A piezoelectric element in the form of a slice constituted by an internal layer of nickel and an external layer of ceramic is secured by welding on the base plate. When voltage is applied to the piezoelectric element, this latter contracts so as to expel the liquid contained in the pump. This pump is of a very different construction than those obtained by photolithographic micromachining of the sealing materials.

EP-A-0 025 005 discloses a micropump comprising at least one flexible membrane, preferably metallic, on the two sides of which are secured two piezoelectric elements. This membrane is mounted on a ceramic wall. By application of voltage to the piezoelectric elements, these latter deform to impart to the membrane a pumping movement. This membrane micropump is also of a type entirely different from that of the micropumps obtained by photolithographic micromachining of sealing materials.

There are also known numerous types of small pumps which utilize extensible resilient pumping membranes, particularly of an elastomer, and by means of which high pumping volumes can be achieved. As example of this type of pump can be cited those used for aquaria. Nevertheless, these pumps are not of the type produced by machining as described above. Moreover, the readily extensible materials used let pass gases or vapors thus limiting the applications to uses in which no hermetic sealing is acceptable. In uses in which the pump assembly comprises electronic components contained in a sealed chamber for example, no vapor can escape from the pump.

With hermetically sealed materials, as silicon which is breakable and which is practically inextensible, it is necessary to find other solutions to the problems described above.

SUMMARY OF THE INVENTION

The object of the present invention is to provide an entirely self-starting micropump completely sealed internally of the micropump and which operates also in a correct manner when air or another gas or compressible fluid enters the internal volume of the micropump.

The micropump is characterized for this purpose by the fact that the inlet control member opens outwardly of the plate on or in which it is located, whilst the outlet control member opens inwardly of the plate on or in which it is located, such that the decrease of internal volume compresses a gas contained in said internal volume at a pressure sufficient to give rise to opening of the outlet control member, so as to obtain a self-starting micropump.

Thus, it is possible to start the micropump without particular apparatus, rapidly and automatically, considering that the air contained in the internal volume is evacuated by the pumping effect itself of the micropump, whilst having the advantage of complete sealing of this internal volume of the micropump.

Preferably, said volume decrease of the pumping chamber is comprised between 30 and 100% of said internal volume, preferably more than 50%, the volumes of said spaces connecting the pumping chamber to the inlet and outlet control members being less than 30% of the internal volume, preferably less than 15%.

There is thus obtained a starting and an evacuation of air which is particularly effective.

According to a preferred embodiment, the movable wall comprises a rigid central portion surrounded by an elastic border of lesser thickness, made of one piece with the rigid central portion, this latter projecting relative to the surface of the movable wall which is opposite the pumping chamber and being adapted to coact with the actuation means.

Such a construction permits very favorable evacuation of the pumping chamber, hence reliable starting. The rigid central portion of the movable wall ensures a precise displacement of this wall, comparable to the movement of a piston. The pressure differences in the pumping chamber give rise to only a slight change in volume thanks to the smaller surface of the elastic border surrounding the rigid central portion.

Desirably, the micropump has at least one third plate secured to the second plate, the actuating means comprising a motor member mounted movably on the third plate, an intermediate member being disposed between said rigid central port and the motor member.

This construction has the advantage of effective actuation. Variations in the shape and in the deformation of the motor member, preferably a piezoelectric member, have no influence on the shape of the deformable wall.

Preferably, the intermediate member comprises a lower surface adapted to enter into contact with said rigid central portion having a surface similar to that of the rigid central portion.

The use of the actuation movement is effected over all the width of the rigid central member which is therefore not subjected to any deformation, which permits a very precise evacuation of the pumping chamber.

According to a preferred modification, the inlet and/or outlet control members of the fluid are constituted by at least one valve comprising two membranes machined in the second plate so as to constitute a V shape in the closed position of the valve, these membranes being adapted to be separated to form an intermediate overture in the open position of the valve.

This type of valve can be of very small size such that the space connecting the valve to the pumping chamber has an extremely reduced volume, which permits greatly reinforcing the self-starting effect of the micropump.

The invention also relates to a micropump arranged for the administration of medications and adapted to be implanted in the body of a patient.

Other advantages will become apparent from the characteristics set forth in the dependent claims and the expository description that follows, of the invention, in greater detail, with the help of drawings which show schematically and by way of example four embodiments.

DESCRIPTION OF THE PREFERRED EMBODIMENTS

In FIGS. 1 to 4, 6 and 7, a same element represented on several figures is designated on each of these latter by the same reference numeral. In the embodiments which will be described, the micropump is provided with one or several inlet valves or with a flow limiter and an outlet valve. It should however be noted that the invention is applicable equally to micropumps comprising several valves disposed between the pumping chamber and the outlet. The micropump can also be provided with a plurality of outlets. The inlet and outlet valves could be replaced by any other inlet or outlet control member for the fluid, such as flow limiters.

It is to be noted that, for purposes of clarity, the thicknesses of various plates comprising the micropump have been greatly exaggerated in the drawings.

Figure 1:
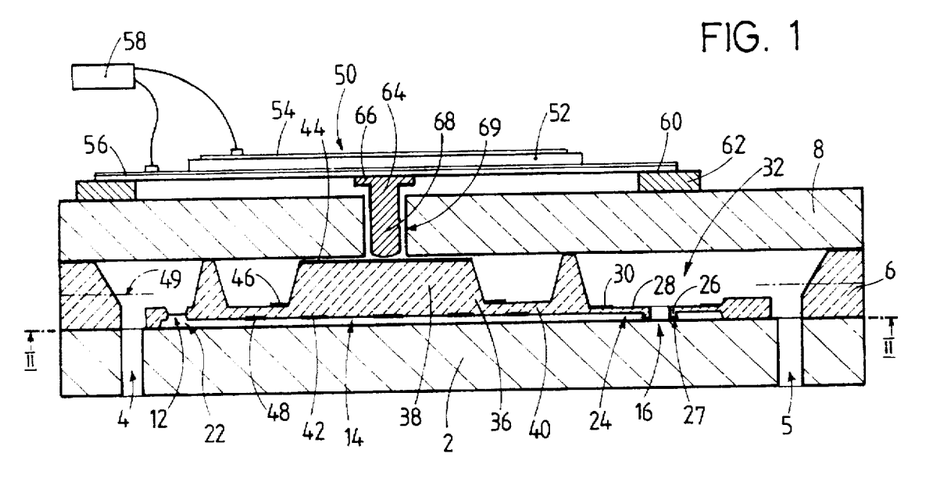
FIG. 1 shows a first embodiment of the invention in cross section on the line I—I of FIG. 2.
Figure 2:
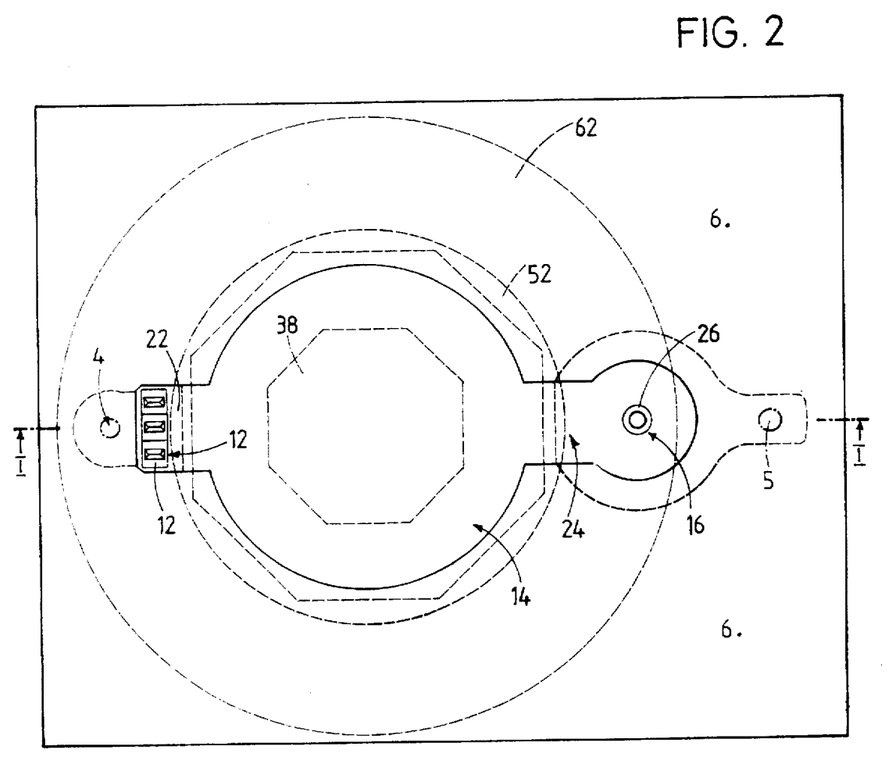
FIG. 2 is a horizontal cross section on the line II—II of FIG. 1.

With reference to FIGS. 1 and 2, the micropump according to the first embodiment comprises a base plate 2, preferably of glass. This base plate 2 is pierced by two channels 4, 5 forming inlet and outlet conduits of the pump.

The inlet conduit 4 can be connected to a reservoir (not shown) in which is located the liquid substance to be pumped, for example a medication to be administered with a precise dosage. In this use, the micropump could be carried on the body of the patient, even be implanted. The outlet conduit 5 could be connected to an injection needle (not shown) for example.

The base plate 2 is surmounted by an intermediate plate 6 of silicon or another material machinable by incising with the aid of photolithographic techniques. It is secured to the base plate 2 by known connection techniques, such as "anodic bonding" or anodic welding comprising a heating to about 300° C. and the application of a voltage difference of about 500V between the plates.

An upper plate 8, preferably of glass, is secured by the same techniques to the intermediate plate 6.

By way of example, the intermediate plate 6 of silicon can have a crystal orientation <100>, so as to be adapted successfully to incision. The plates 2, 6 and 8 are preferably carefully polished. The plates 2, 6 and 8 are then preferably rendered hydrophilic, particularly in the case in which the substance used in the micropump is an aqueous solution. The silicon plate 6 can for this example be immersed in fuming $HNO_3$.

Specifically, the thicknesses of the plates 2, 6 and 8 can be respectively about 1 mm, 0.3 mm and 0.8 mm for a surface dimension of the plates of the order of 15×20 mm.

The inlet or suction conduits 4 and the outlet or discharge conduits 5 are principally connected by three inlet valves 12, a pumping chamber 14 and an outlet valve 16.

Figure 5A:
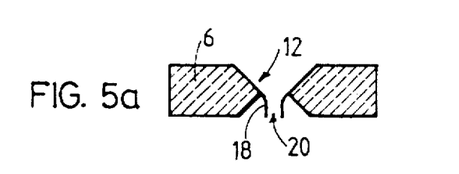
FIGS. 5a) to 5d) show a particular type of valve used, represented in transverse cross sections and in bottom views for the open and closed positions.
Figure 5B:
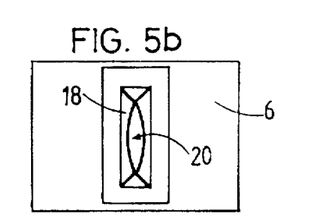
Figure 5C:
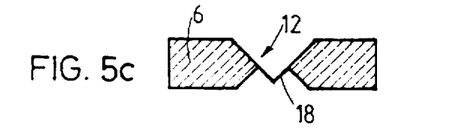
Figure 5D:
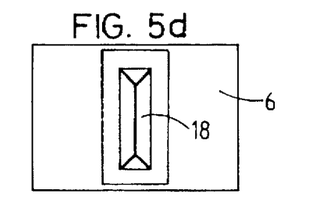

The inlet valves 12 are shown more particularly in FIGS. 5a) to 5d) and each comprise two membranes 18 machined in the silicon plate 6 so as to constitute a V shape in the closed position of the valve (FIGS. 5c) and d)). The membranes 18 are adapted to separate at their junction to form an intermediate opening 20 in the open position of the valve (FIGS. 5a) and b)). This type of valve obtained by micromachining is more particularly described by L. Smith and B. Hök in an article entitled "A silicon self-aligned nonreverse valve" which appeared in "Transducers 91, Digest of Technical Papers", pp. 1049–1051 IEEE catalog No. 91CH2817-5, IEEE, Piscataway, N.J. (1991).

These valves permit a construction of very small size and do not require but a very small volume of connection space 22 for connection to the pumping chamber. The phenomenon of microcavitation which appears in the usual types of valves having a valve coacting with a seat is avoided. Thus, in these valves of the usual type, a great decrease of pressure is observed very locally at the level of the valve seat at the moment of separation of the valve from its seat. This pressure decrease can give rise to the formation of gas microbubbles, when the pressure at this point of the liquid becomes less than the vapor pressure of the latter. This drawback cannot arise with the present type of valve 12 with membranes of V shape because the spacing of the membranes takes place in a sliding manner with fluid flow along the two membranes.

Because of the very small dimension of the three valves, the connection space 22 located below the three inlet valves 12 has a very limited volume and is connected immediately to the pumping chamber 14.

This latter is connected to the outlet valve 16 by a second connection space 24 which surrounds the annular rib 26 of this outlet valve 16. This second connection space 24 preferably has a volume as small as possible.

The outlet valve 16 of conventional type is similarly machined in the silicon plate 6 and comprises a membrane 28 carrying the annular rib 26 covered with an oxide layer 27 giving to the membrane 28 a prestress urging the apex of the rib 26 against the lower plate 2 which serves as a valve seat. Oxide layers 30 applied to the other side of the membrane 28 reinforce this prestress. The rib 26 delimits a compartment 32 externally of the rib 26 and communicating with the outlet conduit 5.

Of course other types of control members for the fluid outlet could equally well be provided, such as valves of the V-shaped membrane type or for example flow limiters.

The pumping chamber 14 is of substantially circular shape. Its volume is controlled by a pumping member 36 constituting a movable or deformable wall of pumping chamber 14. This movable wall is machined in the silicon plate 6 and comprises a rigid central portion 38 that is relatively wide relative to the total width of the pumping membrane 36. The diameter of this central portion 38 varies between 20 and 90% of the diameter of the pumping membrane 36, preferably between 50 and 80%. This rigid central portion 38 has a thickness substantially greater than the annular edge 40 of the pumping membrane. Specifically, the edge 40 has a thickness between 10 and 100 μm, whilst the rigid central portion 38 has a thickness which is by 10 to 50 μm less than the total thickness of the plate 6, which gives for example a thickness of 300 μm.

This pumping membrane 36 comprises on its lower surface facing the plate 2, zones 42 provided with a thin layer of silicon oxide permitting avoiding sticking of the membrane 36 to the plate 2. A thin layer of silicon oxide 44 likewise is provided on the upper surface of the rigid central portion 38 for the same purpose. Silicon oxide layers 46, 48 applied to the two sides of the annular edge 40 are adapted to confer on the membrane a certain prestress (not shown) upwardly in FIG. 2. The rigid central portion 38 and the upper plate 8 with which it coacts constitute abutment elements limiting the suction movement of the pumping membrane 36.

It is to be noted that the inlet valves 12 and outlet valves 16 are all disposed on the same side of an imaginary intermediate surface 49 of the plate 6; the pumping chamber 14 is located on the same side of this intermediate surface. The outlet valve 16, which has a construction different from that of the inlet valves 12, opens in the direction of this intermediate surface 49 whilst the inlet valves 12 open in the opposite direction, downwardly, by moving away from this intermediate surface.

An actuating device 50 for the pumping membrane 36 comprises a motor member in the form of a piezoelectric member 52 provided with electrodes 54, 56 connected to a generator 58 adapted to supply alternating voltage. This element can be one sold by the Philips Company as PXE-52. It is secured by any suitable means such as gluing or welding, on a resilient blade 60 of metal, silicon or other deformable material. This blade 60 is mounted by means of a spacing member 62 on the upper plate 8. The spacing member 62 could be constituted by a support ring of plastic, metal or silicon. It could also be formed by a predetermined thickness of glue or of glass which is of one piece with the plate 8. An intermediate member 64 in the form of a tack can be secured by its head plate 66 by any suitable means, such as gluing or welding, to the resilient blade 60. It acts on the rigid central portion 38 of the pumping membrane 36 because of its vertical rod 68 passing through the upper plate 8 through a hole 69. There can moreover be a small play or a mechanical constraint between the vertical rod 68 and the pumping membrane 36, when the pump is at rest.

The actuating device 50 comprising a piezoelectric element 52 and a resilient blade 60, could also be replaced by a device 3 comprising two or several piezoelectric plates secured together or combined piezoceramic and metallic discs.

Thus, the piezoelectric element 52 is independent of the pumping membrane 36. Historesis effects of the piezoelectric element 52 ("piezocreep") or variations or deterioration of this element have no influence on the shape of the pumping member 36 given that this latter is independent of the piezoelectric element 52 and is moved by the intermediate member 64. This construction permits obtaining a large volume of displaced fluid for a given diameter of the pumping member, given that the rigid central portion 38 acts in the manner of a piston. The machine portions of the micropump can be still further miniaturized whilst maintaining an actuating device of any size, even relatively large. This miniaturization of the machined members permits lowering the cost.

The described micropump comprises an internal volume (Vi) comprising the volume (Vp) of the pumping chamber 14, the volume (Ve) of the connection space 22 delimited on the one hand by inlet valves 12 and connected on the other hand to the pumping chamber 14, and the volume (Vs) of the connection space 24 with the outlet valve, including its annular portion surrounding the annular rib 26. The actuating means 50 displace the movable wall 26 to give rise to periodic variation (ΔVp), decrease then increase of the volume (Vp) of the pumping chamber 14. The decrease of the internal volume (Vi) of the micropump due to the decrease of volume (Vp) of the pumping chamber is such that a gas, for example air, or any other compressible fluid contained in the internal volume of the micropump, is compressed at least to a pressure sufficient to give rise to opening of the outlet valve 16 such that this air may be discharged from the micropump which is thus self-starting.

To obtain this effect, it is necessary that the variation or decrease ($\Delta$Vp) of the volume of the pumping chamber 14, caused by the movement of the movable wall 36, will not be much less than the volume (Vp) of the pumping chamber. Furthermore, the volume (Ve and Vs) of the connection spaces 22 and 24 must be as small as possible, which can be obtained by micromachining.

Preferably, the variation or decrease ($\Delta$Vp) is comprised between 30 and 100% of the internal volume (Vi), preferably more than 50%.

The volume (Ve and Vs) of the connection spaces 22 and 24 together is preferably less than 30% of the internal volume (Vi) and preferably less than 15% of this internal volume.

More particularly, the embodiment could have a movable wall 36 of a diameter of 7 mm with a rigid central portion of a diameter of 5 mm and a vertical displacement of 10 μm. The variation or decrease of the volume ($\Delta$Vp) of the pumping chamber 14 would then be approximately 0.28 mm$^3$. The volume (Vp) of the pumping chamber being 0.38 mm$^3$, that (Ve) of the connection space toward the inlet valves 22 being 0.015 mm$^3$, that (Vs) of the connection space 24 toward the outlet valve being 0.03 mm$^3$. The internal volume (Vi) will be approximately 0.43 mm$^3$.

Thus the variation or decrease ($\Delta$Vp) will be about 65% of the internal volume (Vi) and the volume (Ve+Vs) of the two connection spaces 22, 24 together will be only about 10% of the internal volume (Vi) of the micropump.

Given that the micropump at rest, unstarted, is full of air at a pressure of 1 bar and that this air is then compressed to a volume of 35% of the original volume, a pressure greater than 2.5 bar is generated in the internal volume (Vi) of the micropump.

Given that an internal pressure of 1.5 bar is required to effect opening of the outlet valve 16, the pressure generated within the micropump is quite sufficient to render this latter completely self-starting. Thanks to the rigid central member 38 of a large diameter operating in the manner of a piston and to the very small connection spaces 22 and 24, it is possible to obtain sufficient pressures within the micropump to permit self-starting.

This is not the case with known micropumps which generally comprise a space of a fairly large size on the internal side of the inlet valve. Thus, the internal volume is generally of the order of 3 mm$^3$, whilst the variation of volume due to the pumping movement is about 0.1 mm$^3$ with a conventional pumping membrane of a diameter of 7 mm. Such a micropump thus cannot operate as soon as a gas partially or completely fills its internal volume. This great drawback of the operation and starting is entirely avoided thanks to the present invention. Similarly, during complete mounting of the pumping membrane 36, the increase in internal volume (Vi) of the micropump due to the increase of the volume (Vp) of the pumping chamber 14 is such that the gas, namely air, remaining in the internal volume of the micropump after closure of the outlet valve 16 is decompressed to a sufficiently low pressure to give rise to the opening of the inlet valve or valves 12.

The central rigid member 36, which is thicker, adapted to enter into contact with the upper plate 8, comprises an abutment element opposite the abutment elements constituted by regions of silicon oxide 42 entering into contact with the base plate 2.

The suction and expulsion movements of the pumping membrane 36 are thus mechanically controlled from the upper and lower side. This permits obtaining a quantity of pumped substance which is very precise upon each movement cycle of the membrane. The rigid central portion 36 is comparable to a piston whose movement is precisely defined, given that the annular edge 40 of the pumping membrane 36 has a relatively small surface compared to the total surface of the pumping membrane 36, the pressure differences in the pumping chamber 14 give rise to only small changes of volume below the pumping member 36.

Moreover, the regions of oxide 42 avoid a sticking effect of the pumping membrane 36 during anodic welding or a suction effect of this membrane, when the latter displaces from the lowest position upwardly.

Electric contacts or electrodes (not shown) can be disposed facing each other on the rigid central portion 38 and on the lower surface of the upper plate 8. These contacts are then extended inwardly of the pump and connected to an electric circuit (not shown) permitting controlling the operation of the pumping membrane 36 and the intake of the fluid. Suitable circuits are for example disclosed in European patent application No. 0 498 863.

The general manner of operation of this pump is like that described in the article by H. Van Lintel et al., entitled "A piezoelectric micropump based on micromachining of silicon" which appeared in "Sensor and Actuators", No. 15 (1988), pp. 153 to 167.

Relative to this known type of micropump, the micropump according to the present invention therefore permits obtaining a self-starting which will be certain and reliable. Moreover, the micropump has a very precise dosage upon each alternating movement, a dosage which is practically independent of the pressure prevailing in the inlet and outlet conduits, and independent of the performance of the piezoelectric element and of the deterioration and historesis phenomena known to occur in this type of actuating device. Moreover, the movement of the pumping membrane is controlled in a precise fashion both by the rigid intermediate member 38 and by the oxide regions 42. The flow is thus defined by the machining characteristics of the pumping membrane 36 and by the frequency of the actuating device.

This type of pump permits the use of piezoelectric elements having fairly wide variations in their characteristics. Moreover, it is not necessary to calibrate the pumps for each element used.

Because of the external securement of the element, this latter can be easily replaced in case of defect.

Of course the embodiment described above is not limitative and it can be the subject of all desirable modifications within the scope of the invention. In particular, the construction of the valves and the arrangement of the valves and of the outlet and inlet conduits, as well as the pumping chamber, could be very different. The outlet valve could equally well be of the type with two members in a V. The pumping chamber and these valves or control members of the fluid could also be arranged in part or in whole on the base plate, if that appeared preferable. The valves or control members are thus disposed on the side of the plate on which they are machined which is nearest the pumping chamber, the inlet valves 12 opening externally of the plate on which they are located, whilst the outlet valves 16 open inwardly of the plate on which they are located. The distribution of the oxide regions could be adapted to the desired parameters for the valves and the pumping. The actuating device could have a motor member of another type than a piezoelectric element.

The intermediate member 64 could be of one piece with the resilient blade 60 or even with the piezoelectric element. It could also be freely disposed between the elastic blade and the pumping member.

The pump could moreover have one or several screws passing through the upper plate 8 and coacting at their end with the rigid central portion 8. These screws thus constitute adjustable abutment elements permitting adjusting the amplitude of movement during suction.

Adjustment screws could also be mounted on the blade 60. Moreover, it would be possible to mount adjustment screws in the head plate 66 of the intermediate member.

Figure 3:
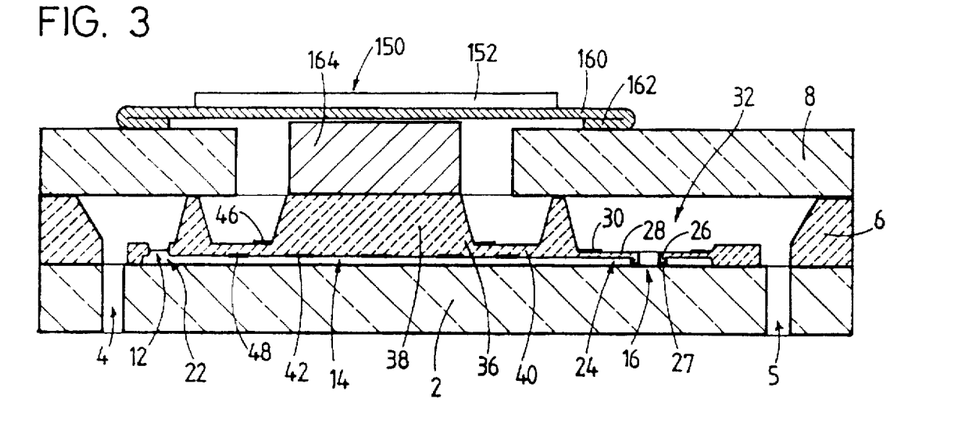
FIG. 3 shows a second embodiment in cross section.

The second embodiment shown in FIG. 3 differs from the first embodiment solely by the construction of the actuating device. Because of this, analogous elements in the two embodiments bear the same reference numerals and will not be described in detail.

This second embodiment also comprises a base plate 2 pierced by inlet conduits 4 and outlet conduits 5 and an upper plate 8. Between these plates 2 and 8 is inserted the intermediate plate 6 of silicon machined by photolithographic techniques to obtain one or several inlet valves 12 and outlet valves 16 and a pumping chamber 14.

Thin oxide layers 27, 30, 46, 48 permit obtaining predetermined prestress in the machined silicon membrane.

The pumping chamber 14 is of substantially circular shape and connected by two connecting spaces 22, 24 to the inlet and outlet valves. Machined in the silicon plate 6, the pumping membrane 36 in the form of a movable deformable wall comprises a rigid central portion 38 which is thicker.

The actuating device 150 has a resilient metal plate 160 having folded under edges 162 forming spacing elements secured to the upper surface of the plate 8. A motor member in the form of a piezoelectric member 152 is secured by welding or gluing to the blade 160. It acts because of an intermediate member 164 on the rigid central portion 38 of the pumping membrane 36. This intermediate member 164 has a cross section and a lower surface similar to that of the rigid central portion 38 and is secured to this latter by any suitable means, such as anodic welding or gluing. Thanks to this intermediate member 164 of considerable diameter, the pumping membrane 36 is displaced vertically without giving rise to deformation of the greater part of its surface. The evacuation of the pumping chamber 14 is thus particularly effective, which increases further the self-starting effect of the microvalve for a given geometry of the internal volume (Vi). Moreover, the construction and mounting are simple, which permits reducing the price of the micropump.

Figure 4:
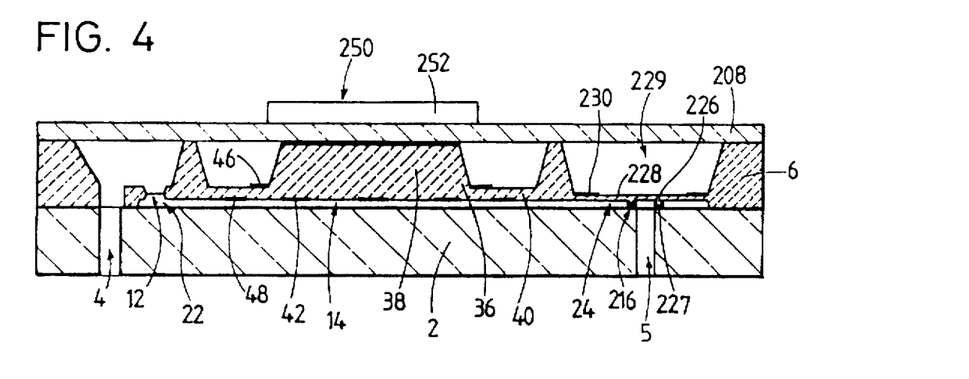
FIG. 4 shows a third embodiment in cross section.

The third embodiment shown in FIG. 4 differs from the first and second embodiments particularly by the construction of the outlet valve 216 and the actuating device 250. Because of this, analogous elements in the three embodiments bear the same reference numerals and will not be described in detail.

This third embodiment also comprises a base plate 2 provided with an inlet conduit 4 and an outlet conduit 5 and an upper plate 8. Between these plates 2 and 8 is inserted the intermediate plate 6 of silicon machined by photolithographic techniques to obtain one or several inlet valves 12 and outlet valves 216 and a pumping chamber 14. Thin layers of oxide 227, 230, 46 and 48 permit obtaining predetermined prestresses in the machined silicon membrane.

The pumping member is also of circular shape and connected by connecting spaces 22 and 24 to the inlet and outlet valves.

The upper plate 208 of glass is in this embodiment of a small thickness of the order of 0.2 mm so as to be elastically deformed by the piezoelectric element 252, which is fixed by gluing to its upper surface. The piezoelectric element 52 acts by elastic deformation of the glass plate on the rigid central portion 38 to obtain the pumping movement.

This construction does not require piercing of the glass plate, hence a more rapid and easy mounting.

The outlet valve 216 comprises an unpierced membrane 228 having an annular rib 226 disposed about the outlet channel 5 and covered with a fine layer of silicon oxide 227.

This embodiment comprises also a chamber 229 disposed between the membrane 228 and the upper plate 208. This chamber 229 could be connected to the inlet conduit 4 and constitute protection against overpressure at the inlet of the microvalve closing the outlet conduit 5 in case of overpressure. It could also be connected to detection members for the operation of the valve. Finally, it could also be sealed or connected to the ambient air. This construction requires very good alignment between the annular rib 226 and the outlet conduit 5 which should have a small diameter.

Instead of an inlet valve, the micropumps described could have as a control for the incoming fluid, a flow limiter formed by a conduit of very small cross section connecting the inlet conduit directly to the pumping chamber. The connecting space between these two elements would thus have a very small volume, which is particularly favorable for self-starting.

The actuating device constituted by a piezoelectric element could also be glued directly on the pumping membrane and connected to a generator adapted to supply alternating voltage.

The frequency of actuation of the piezoelectric element will be in this embodiment with a flow limiter, higher, namely between 10 and 100 Hertz instead of 1 to 10 Hertz for embodiments with an inlet valve. Considering this higher frequency and the small flow cross section of the flow limiter, there is used a self-starting current adapted to evacuate the gas contained in the internal volume (Vi) of the micropump toward the outlet conduit. Of course, in this variant also, the variation ($\Delta Vp$) of the volume of the pumping chamber 14 should not be much less than the volume (Vp) of the pumping chamber and the internal volume (Vi) of the micropump. The volumes (Ve and Vs) of the connection spaces toward the limiter and toward the outlet valve must be as small as possible to obtain effective self-starting.

Figure 6:
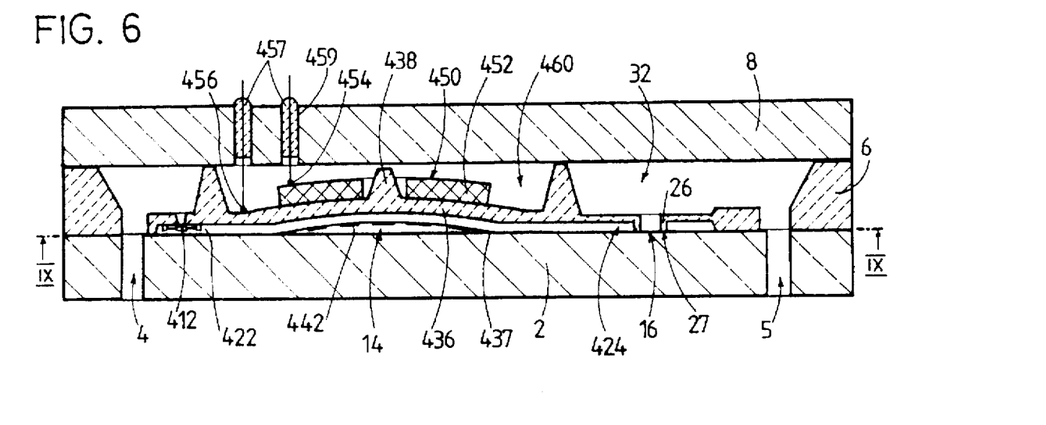
FIG. 6 shows a fourth embodiment in cross section on the line VIII—VIII of FIG. 7.
Figure 7:
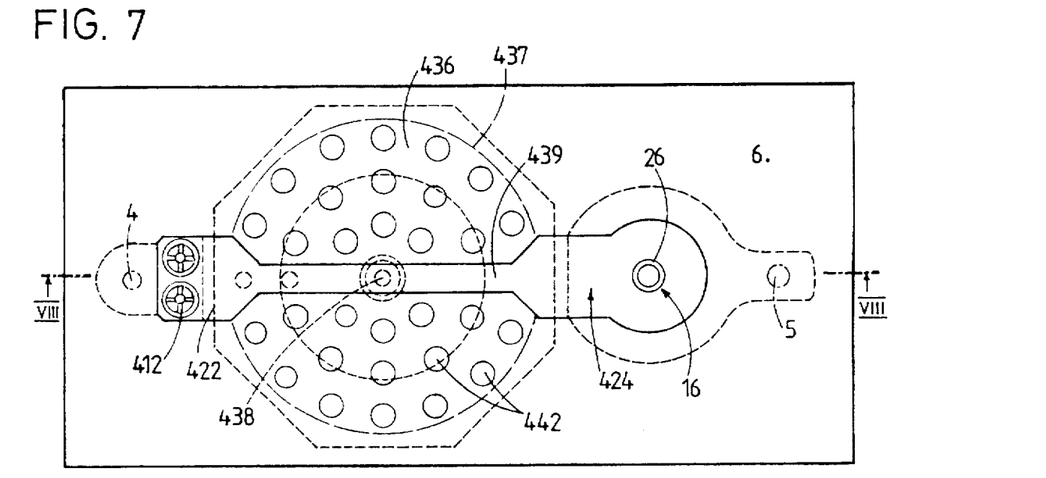
FIG. 7 is a view in horizontal cross section on the line IX—IX of FIG. 6.
Figure 8A:
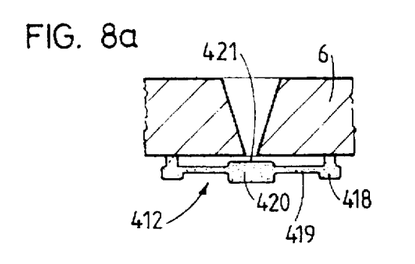
FIGS. 8a and 8b show another particular type of valve used, in transverse cross section and in plan view.
Figure 8B:
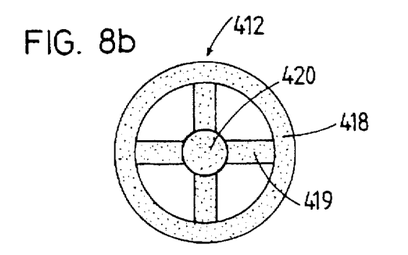

The fourth embodiment shown in FIGS. 6 to 8 comprises, as in the first embodiment, a base plate 2 of glass with inlet and outlet conduits 5, an intermediate plate 6 of silicon machined by incision and an upper plate 8 preferably of glass. This embodiment is provided with two inlet valves 412 which are of the type disclosed in the article by Shoji et al., "Technical Digest of the 7th Sensor Symposium", 1988, pp. 217 to 220. With reference to FIG. 8, these polycrystalline silicon valves are obtained by surface micromachining techniques. They comprise an annular structure 418 connected to the plate 6 and connected by four arms 419 to a central closure member 420 adapted to coact with a hole 421 provided in the plate 6.

The outlet valve 16 is of the same type as that disclosed in FIG. 1. The pumping membrane 436 has in this case however, in the rest position, an upwardly bulging shape and comprises a central portion 438 of smaller diameter. Its internal surface directed toward the pumping chamber 14 is provided with a plurality of circular regions 442 of silicon oxide adapted to prevent sticking or suction of the membrane 436. The broken line 437 indicates the limit of contact between the membrane 436 and the base plate 2. This membrane 436 comprises moreover a hollow 439 connecting the connection space 422 to the connection space 424. This hollow 439 is also adapted to avoid a suction of the membrane 436. It could of course also be provided in the base plate 2.

The actuating device 450 comprises a piezoelectric element 452 of annular shape secured to the membrane 436 about its central portion 438. Two electrodes 454 and 456 are connected by wires 457 to an alternating voltage generator. The openings 459 in the plate 8 are closed hermetically by for example at least one epoxy glue or by a weld.

When the piezoelectric element 452 is actuated, the membrane 436 displaces downwardly of FIG. 6 to achieve a substantially flat shape, which permits obtaining an excellent ratio of compression of the pumping chamber 14 which thus has a very small residual volume. The height of the bulge of the pumping membrane 436 therefore corresponds substantially to the pumping displacement of this membrane.

This bulged shape of the membrane 436 can be obtained by placing under vacuum the chamber 460 located above the hermetically closed membrane. It could also be obtained by applying to its upper surface an oxide layer inducing a prestress suitable deformation.

It is to be noted that a membrane that bulges thus upwardly could also be very advantageous in the other embodiments described above. Similarly, the valves 412 of polycrystalline silicon could also be used in the framework of the other embodiments and as the outlet valve. The micromachining of these valves could also be obtained with other materials, such as silicon nitride or metals used in electroforming. The central member 438 serving as an opening abutment could also be omitted, but in the present case it is useful to increase the pumping precision and as a safety element to avoid rupture of the pumping membrane 436 during overpressure in the inlet channel 4.

Thus, the disclosed embodiments permit, thanks to a self-starting effect, evacuating air entering the pump by observing only a temporary decrease of the pumping flow rate until all the air has been driven out the outlet conduit of the micropump.

The embodiments described are particularly adapted for the administration of medications and for implantation in the body of a patient.

What is claimed:

1. A micropump comprising:
    a base plate;
        a second plate secured to the base plate, thereby defining a pumping chamber having a volume and a movable wall machined in one of the plates;
    inlet and outlet control members in direct connection with the pumping chamber, said control members being located on or in at least one of the two plates, at least one of the two plates being machined by photolithographic micromachining technique from a hermetic material, said control members and said pumping chamber defining connecting spaces therebetween, the connecting spaces having volumes, an internal volume comprising the volume of the pumping chamber and the volumes of the connecting spaces; and
    actuating means for displacing said movable wall to cause a periodic decrease and increase of said internal volume,
    the inlet control member opening towards an outside of the plate on or in which said inlet control member is located, the outlet control member opening towards an inside of the plate on or in which it is located, such that the decrease of internal volume compresses a fluid contained in said internal volume to a pressure sufficient to effect opening of the outlet control member, so as to obtain a self-priming micropump.

2. The micropump according to claim 1, wherein the pumping chamber and the connecting spaces are shaped such that the increase of internal volume of the micropump due to the increase of volume of the pumping chamber is such that pressure of fluid remaining in the micropump after closure of the outlet control member of the fluid is sufficiently low so as to open the inlet control member for the fluid.

3. The micropump according to claim 1, wherein the decrease of volume of the pumping chamber is comprised between 30 and 100% of said internal volume, the volumes of said connecting spaces of the pumping chamber to the inlet and outlet control members being less than 30% of the internal volume.

4. The micropump according to claim 1, wherein the pumping chamber is disposed on one side of an intermediate surface of the plate in or on which said pumping chamber is defined, each of the inlet and outlet control members being disposed in or on the side of the plate on which said each of the control members is machined which is nearest the pumping chamber.

5. The micropump according to claim 1, wherein the inlet member has a different construction from that of the outlet member.

6. The micropump according to claim 1, wherein the movable wall comprises a rigid central portion surrounded by a resilient border of lesser thickness, said movable wall being made of one piece with the rigid central portion, the rigid central portion projecting relative to a surface of the movable wall which is opposite the pumping chamber and being adapted to coact with said actuating means.

7. The micropump according to claim 6, wherein said rigid central portion and said movable wall have respective widths, the width of said rigid central portion varying between 20 and 90% of the width of the movable wall.

8. The micropump according to claim 6, further comprising a third plate having a sufficiently small thickness so that said third plate is deformable elastically by the actuating means which is mounted on an external surface of the third plate, an internal surface of the third plate adapted to coact with the rigid central portion to displace the movable wall.

9. The micropump according to claim 1, wherein the actuating means comprise a piezoelectric element mounted directly on said movable wall.

10. The micropump according to claim 1, further comprising a third plate, wherein the movable wall comprises a rigid central portion, arranged so as to enter into contact with said third plate to constitute an abutment element limiting suction of the fluid by the movable wall.

11. The micropump according to claim 1, wherein at least one of the inlet and outlet control members includes a valve comprising two membranes machined in the second plate so as to constitute a V shape in the closed position of the valve, the two membranes being adapted to be separated to form an intermediate opening in the open position of the valve.

12. The micropump according to claim 1, wherein at least one of the inlet and outlet control members for the fluid comprises a valve of a material machined by surface micromachining.

13. A micropump comprising:
a base plate;
a second plate secured to the base plate, thereby defining a pumping chamber having a volume and a movable wall machined in one of the base plate and the second plate, the movable wall having a rigid control portion;
a third plate secured to the second plate;
inlet and outlet control members in direct connection with the pumping chamber, said control members being located on or in at least one of the base plate and the second plate, at least one of the base plate and the second plate being machined by photolithographic micromachining technique from a hermetic material, said control members and said pumping chamber defining connecting spaces therebetween, the connecting spaces having volumes, an internal volume comprising the volume of the pumping chamber and the volumes of the connecting spaces; and
actuating means for displacing said movable wall to cause a periodic decrease and increase of said internal volume, said actuating means including a motor member mounted movably on the third plate, an intermediate member located between said rigid central portion and said motor member,
the inlet control member opening towards an outside of the plate on or in which said inlet control member is located, the outlet control member opening towards an inside of the plate on or in which it is located, such that the decrease of internal volume compresses a fluid contained in said internal volume to a pressure sufficient to effect opening of the outlet control member, so as to obtain a self-priming micropump.

14. The micropump according to claim 13, wherein the motor member is mounted movably on the external surface of said third plate, said intermediate member passing through the third plate through an opening.

15. The micropump according to claim 14, wherein the motor member is a piezoelectric element mounted by a spacing member on an external surface of the third plate.

16. The micropump according to claim 13, wherein the intermediate member comprises a plate head secured to the motor member and a rod passing through the third plate and acting by its end on the movable wall.

17. The micropump according to claim 13, wherein the intermediate member comprises a lower surface adapted to enter into contact with said rigid central portion, the lower surface having a shape similar to that of the rigid central portion.

18. The micropump according to claim 13, further comprising a protection chamber, wherein the control member comprises a valve membrane having an annular rib urged against a plate located facing the same and surrounding an outlet of the micropump, this latter comprising the protection chamber delimited by a surface of the valve membrane opposite the annular rib and the third plate or the base plate, the protection chamber being adapted to form an active or control cavity of the micropump.

19. A micropump comprising:
a base plate;
a second plate secured to the base plate, thereby defining a pumping chamber having a volume and a movable wall machined in one of the base plate and the second plate, the movable wall having in its rest position a shape bulging outwardly of the pumping chamber;
a third plate secured to the second plate;
inlet and outlet control members in direct connection with the pumping chamber, said control members being located on or in at least one of the base plate and the second plate, at least one of the base plate and the second plate being machined by photolithographic micromachining technique from a hermetic material, said control members and said pumping chamber defining connecting spaces therebetween, the connecting spaces having volumes, an internal volume comprising the volume of the pumping chamber and the volumes of the connecting spaces; and
actuating means for displacing said movable wall to cause a periodic decrease and increase of said internal volume, said actuating means including a motor member mounted movably on the third plate, an intermediate member located between said rigid central portion and said motor member,
the inlet control member opening towards an outside of the plate on or in which said inlet control member is located, the outlet control member opening towards an inside of the plate on or in which it is located, such that the decrease of internal volume compresses a fluid contained in said internal volume to a pressure sufficient to effect opening of the outlet control member, so as to obtain a self-priming micropump.

20. The micropump according to claim 19, wherein the height of the bulge corresponds substantially to the displacement of the pump effectuated by the movable wall.

21. The micropump according to claim 19, further comprising a layer of a material applied on a surface of the movable wall, wherein the bulge of the movable wall is produced by at least one of a vacuum existing in a chamber located on the rear surface of the movable wall and a presence of the layer of a material applied on the surface of the movable wall inducing a deforming prestress.

22. A micropump comprising:
a base plate;
a second plate secured to the base plate, thereby defining a pumping chamber having a volume and a movable wall machined in one of the base plate and the second plate, a surface of the movable wall, which is directed toward the interior of the pumping chamber, being adapted to come into abutment against a facing plate to limit movement of expulsion of fluid in said pumping chamber;
a third plate secured to the second plate;
inlet and outlet control members in direct connection with the pumping chamber, said control members being located on or in at least one of the base plate and the second plate, at least one of the base plate and the second plate being machined by photolithographic micromachining technique from a hermetic material, said control members and said pumping chamber defining connecting spaces therebetween, the connecting spaces having volumes, an internal volume comprising the volume of the pumping chamber and the volumes of the connecting spaces; and
actuating means for displacing said movable wall to cause a periodic decrease and increase of said internal volume, said actuating means including a motor member mounted movably on the third plate, an intermediate member located between said rigid central portion and said motor member,
the inlet control member opening towards an outside of the plate on or in which said inlet control member is located, the outlet control member opening towards an inside of the plate on or in which it is located, such that the decrease of internal volume compresses fluid contained in said internal volume to a pressure sufficient to effect opening of the outlet control member, so as to obtain a self-priming micropump.

23. A micropump comprising:

a base plate;

a second plate secured to the base plate, thereby defining a pumping chamber having a volume and a movable wall machined in one of the base plate and the second plate, surfaces of the movable wall comprising regions including a material for avoiding sticking of said surfaces of the movable wall to the plate located in facing relation;

a third plate secured to the second plate;

inlet and outlet control members in direct connection with the pumping chamber, said control members being located on or in at least one of the base plate and the second plate, at least one of the base plate and the second plate being machined by photolithographic micromachining technique from a hermetic material, said control members and said pumping chamber defining connecting spaces therebetween, the connecting spaces having volumes, an internal volume comprising the volume of the pumping chamber and the volumes of the connecting spaces; and actuating means for displacing said movable wall to cause a periodic decrease and increase of said internal volume, said actuating means including a motor member mounted movably on the third plate, an intermediate member located between said rigid central portion and said motor member, the inlet control member opening towards an outside of the plate on or in which said inlet control member is located, the outlet control member opening towards an inside of the plate on or in which it is located, such that the decrease of internal volume compresses a fluid contained in said internal volume to a pressure sufficient to effect opening of the outlet control member, so as to obtain a self-priming micropump.

24. A micropump comprising:

a base plate;

a second plate secured to the base plate, thereby defining a pump chamber, the pumping chamber having a volume and a movable wall machined in one of the plates;

inlet and outlet control members in direct connection with the pumping chamber, said control members being located on or in at least one of the two plates, at least one of these plates being machined by photolithographic micromachining technique from a sealing material, said control members and said pumping chamber defining connecting spaces therebetween, the connecting spaces having volumes; an internal volume including the volume of the pumping chamber and the volumes of connecting spaces; and actuating means for displacing said movable wall to cause a periodic decrease and increase of said internal volume, the inlet control member opening towards an external direction with respect to a medium plane of the plate on or in which it is located, the outlet control member opening towards an internal direction with respect to a medium plane of the plate on or in which it is located, such that the decrease of internal volume compresses a fluid contained in said internal volume to a pressure sufficient to effect opening of the outlet control member, so as to obtain a self-priming micropump.

* * * * *